United States Patent
Wurth et al.

(10) Patent No.: US 11,420,062 B2
(45) Date of Patent: Aug. 23, 2022

(54) NEUROSTIMULATION SYSTEM FOR CENTRAL NERVOUS STIMULATION (CNS) AND PERIPHERAL NERVOUS STIMULATION (PNS)

(71) Applicant: ECOLE POLYTECHNIQUE FEDERALE DE LAUSANNE (EPFL), Lausanne (CH)

(72) Inventors: Sophie Wurth, Lausanne (CH); Grégoire Courtine, Lausanne (CH); Silvestro Micera, Genèva (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 278 days.

(21) Appl. No.: 15/926,554

(22) Filed: Mar. 20, 2018

(65) Prior Publication Data
US 2018/0280700 A1  Oct. 4, 2018

(30) Foreign Application Priority Data
Mar. 28, 2017 (EP) .................................. 17163191

(51) Int. Cl.
*A61N 1/36* (2006.01)
*A61B 5/11* (2006.01)
(Continued)

(52) U.S. Cl.
CPC ........ *A61N 1/36139* (2013.01); *A61B 5/0031* (2013.01); *A61B 5/1124* (2013.01); *A61B 5/24* (2021.01); *A61B 5/389* (2021.01); *A61B 5/4836* (2013.01); *A61B 5/6829* (2013.01); *A61B 5/7217* (2013.01); *A61N 1/36003* (2013.01);
(Continued)

(58) Field of Classification Search
CPC .................. A61N 1/36067; A61N 1/36003
See application file for complete search history.

(56) References Cited

U.S. PATENT DOCUMENTS 6,366,813 B1  4/2002  DiLorenzo
6,878,112 B2  4/2005  Linberg et al.
(Continued)

FOREIGN PATENT DOCUMENTS

EP    2868343 A1    5/2015
WO    0234331 A2    5/2002
(Continued)

OTHER PUBLICATIONS

Navarro, X. et al., "A critical review of interfaces with the peripheral nervous system for the control of neuroprostheses and hybrid bionic systems," Journal of the Peripheral Nervous System, vol. 10, No. 3, Sep. 2005, 30 pages.
(Continued)

*Primary Examiner* — Michael W Kahelin
(74) *Attorney, Agent, or Firm* — McCoy Russell LLP

(57) ABSTRACT

The present disclosure relates to a neuromodulation and/or neurostimulation system comprising at least the following components: at least one sensing unit, at least control unit, at least one stimulation unit, at least one Central Nervous System (CNS) stimulation module, at least one Peripheral Nervous System (PNS) stimulation module, wherein at least one of the components of the neuromodulation and/or neurostimulation system is implantable.

18 Claims, 7 Drawing Sheets

(51) Int. Cl.
| | |
|---|---|
| A61B 5/00 | (2006.01) |
| A61N 1/04 | (2006.01) |
| A61B 5/24 | (2021.01) |
| A61B 5/389 | (2021.01) |
| A61N 1/05 | (2006.01) |
| A61B 5/296 | (2021.01) |

(52) U.S. Cl.
CPC ..... *A61N 1/36062* (2017.08); *A61N 1/36132* (2013.01); *A61B 5/112* (2013.01); *A61B 5/296* (2021.01); *A61B 5/4082* (2013.01); *A61B 2560/0266* (2013.01); *A61B 2562/0219* (2013.01); *A61B 2562/0247* (2013.01); *A61N 1/0452* (2013.01); *A61N 1/0456* (2013.01); *A61N 1/0551* (2013.01)

(56) References Cited

U.S. PATENT DOCUMENTS

| | | | |
|---|---|---|---|
| 7,149,773 | B2 | 12/2006 | Haller et al. |
| 7,353,064 | B2* | 4/2008 | Gliner ............... A61N 1/36082 607/45 |
| 7,623,928 | B2* | 11/2009 | DiLorenzo ......... A61B 5/04001 607/45 |
| 7,742,037 | B2 | 6/2010 | Sako et al. |
| 8,326,569 | B2 | 12/2012 | Lee et al. |
| 2002/0052539 | A1 | 5/2002 | Haller et al. |
| 2007/0004567 | A1 | 1/2007 | Shetty et al. |
| 2007/0179534 | A1* | 8/2007 | Firlik ....................... A61B 5/16 607/3 |
| 2007/0293910 | A1 | 12/2007 | Strother et al. |
| 2009/0221928 | A1* | 9/2009 | Einav ................... A61B 5/0484 600/544 |
| 2013/0123568 | A1 | 5/2013 | Hamilton et al. |
| 2016/0279418 | A1 | 9/2016 | Courtine et al. |

FOREIGN PATENT DOCUMENTS

| | | |
|---|---|---|
| WO | 2007047852 A2 | 4/2007 |
| WO | 2012080964 A1 | 6/2012 |

OTHER PUBLICATIONS

Courtine, G. et al., "Transformation of nonfunctional spinal circuits into functional states after the loss of brain input," Nature Neuroscience, vol. 12, No. 10, Oct. 2009, Published Online Sep. 20, 2009, 12 pages.
Capogrosso, M. et al., "A Computational Model for Epidural Electrical Stimulation of Spinal Sensorimotor Circuits," Journal of Neuroscience, vol. 33, No. 49, Dec. 4, 2013, 15 pages.
Wenger, N. et al., "Closed-loop neuromodulation of spinal sensorimotor circuits controls refined locomotion after complete spinal cord injury," Science Translational Medicine, vol. 6, No. 255, Sep. 24, 2014, 10 pages.
Moraud, E. et al., "Mechanisms Underlying the Neuromodulation of Spinal Circuits for Correcting Gait and Balance Deficits after Spinal Cord Injury," Neuron, vol. 89, No. 4, Feb. 17, 2016, Published Online Feb. 4, 2016, 16 pages.
Guyatt, G. et al., "The 6-minute walk: a new measure of exercise capacity in patients with chronic heart failure," Canadian Medical Association Journal, vol. 132, No. 8, Apr. 15, 1985, 5 pages.
Lovely, R. et al., "Effects of Training on the Recovery of Full-Weight-Bearing Stepping in the Adult Spinal Cat," Experimental Neurology, vol. 92, No. 2, May 1986, 15 pages.
Barbeau, H. et al., "Recovery of locomotion after chronic spinalization in the adult cat," Brain Research, vol. 412, No. 1, May 26, 1987, 12 pages.
Colgate, E. et al., "An Analysis of Contact Instability in Terms of Passive Physical Equivalents," Proceedings of the 1989 IEEE International Conference on Robotics and Automation, May 14, 1989, Scottsdale, Arizona, 6 pages.
Wernig, A. et al., "Laufband locomotion with body weight support improved walking in persons with severe spinal cord injuries," Paraplegia, vol. 30, No. 4, Apr. 1992, 10 pages.
Winter, D. et al., "An integrated EMG/biomechanical model of upper body balance and posture during human gait," Progress in Brain Research, vol. 97, Chapter 32, Available as Early as Jan. 1, 1993, 9 pages.
Wernig, A. et al., "Laufband Therapy Based on 'Rules of Spinal Locomotion' is Effective in Spinal Cord Injured Persons," European Journal of Neuroscience, vol. 7, No. 4, Apr. 1995, 7 pages.
Pratt, G. et al., "Stiffness Isn't Everything," Proceedings of the Fourth International Symposium on Experimental Robotics (ISER '95), Jun. 30, 1995, Stanford, California, 6 pages.
Basso, D. et al., "MASCIS Evaluation of Open Field Locomotor Scores: Effects of Experience and Teamwork on Reliability," Journal of Neurotrauma, vol. 13, No. 7, Jul. 1996, 17 pages.
Harkema, S. et al., "Human Lumbosacral Spinal Cord Interprets Loading During Stepping," Journal of Neurophysiology, vol. 77, No. 2, Feb. 1, 1997, 15 pages.
Brosamle, C. et al., "Cells of Origin, Course, and Termination Patterns of the Ventral, Uncrossed Component of the Mature Rat Corticospinal Tract," The Journal of Comparative Neurology, vol. 386, No. 2, Sep. 22, 1997, 11 pages.
Kakulas, B., "A Review of the Neuropathology of Human Spinal Cord Injury with Emphasis on Special Features," Proceedings of the Donald Munro Memorial Lecture at the American Paraplegia Society 44th Annual Conference, Sep. 9, 1998, Las Vegas, Nevada, 6 pages.
Hashtrudi-Zaad, K. et al., "On the Use of Local Force Feedback for Transparent Teleoperation," Proceedings of the 1999 IEEE International Conference on Robotics and Automation, May 10, 1999, Detroit, Michigan, 7 pages.
Yoshida, K. et al., "Intrafascicular electrodes for stimulation and recording from mudpuppy spinal roots," Journal of Neuroscience Methods, vol. 96, No. 1, Mar. 1, 2000, 9 pages.
Kirkwood, P., "Neuronal Control of Locomotion: From Mollusc to Man—G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Aug. 1, 2000, Published Online Jul. 17, 2000, 2 pages.
Pratt, J. et al., "Series elastic actuators for high fidelity force control," Industrial Robot: An International Journal, vol. 29, No. 3, Available as Early as Jan. 1, 2002, 13 pages.
Steward, O. et al. "False Resurrections: Distinguishing Regenerated from Spared Axons in the Injured Central Nervous System," The Journal of Comparative Neurology, vol. 459, No. 1, Apr. 21, 2003, 8 pages.
Pearson, K., "Generating the walking gait: role of sensory feedback," Progress in Brain Research, vol. 143, Chapter 12, Published Online Nov. 28, 2003, 7 pages.
Bareyre, F. et al., "The injured spinal cord spontaneously forms a new intraspinal circuit in adult rats," Nature Neuroscience, vol. 7, No. 3, Mar. 2004, Published Online Feb. 15, 2004, 9 pages.
Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, Mar. 15, 2004, 11 pages.
Liu, J. et al., "Stimulation of the Parapyramidal Region of the Neonatal Rat Brain Stem Produces Locomotor-Like Activity Involving Spinal 5-HT7 and 5-HT2A Receptors," Journal of Neurophysiology, vol. 94, No. 2, Aug. 1, 2005, Published Online May 4, 2005, 13 pages.
Timoszyk, W. et al., "Hindlimb loading determines stepping quantity and quality following spinal cord transection," Brain Research, vol. 1050, No. 1-2, Jul. 19, 2005, Published Online Jun. 24, 2005, 10 pages.
Wernig, A., "'Ineffectiveness' of Automated Locomotor Training," Archives of Physical Medicine and Rehabilitation, vol. 86, No. 12, Dec. 2005, 2 pages.

(56) References Cited

OTHER PUBLICATIONS

Nessler, J. et al., "A Robotic Device for Studying Rodent Locomotion After Spinal Cord Injury," IEEE Transactions on Neural Systems and Rehabilitation Engineering, vol. 13, No. 4, Dec. 12, 2005, 10 pages.
Reinkensmeyer, D. et al., "Tools for understanding and optimizing robotic gait training," Journal of Rehabilitation Research & Development, vol. 43, No. 5, Aug. 2006, 14 pages.
Frey, M. et al., "A Novel Mechatronic Body Weight Support System," IEEE Transactions on Neural Systems and Rehabilitation Engineering, vol. 14, No. 3, Sep. 18, 2006, 11 pages.
Cai, L. et al., "Implications of Assist-as-Needed Robotic Step Training after a Complete Spinal Cord Injury on Intrinsic Strategies of Motor Learning," The Journal of Neuroscience, vol. 26, No. 41, Oct. 11, 2006, 5 pages.
Courtine, G. et al., "Can experiments in nonhuman primates expedite the translation of treatments for spinal cord injury in humans?," Nature Medicine, vol. 13, No. 5, May 2007, 13 pages.
Drew, T. et al., "Cortical mechanisms involved in visuomotor coordination during precision walking," Brain Research Reviews, vol. 57, No. 1, Jan. 2008, Published Online Aug. 22, 2007, 13 pages.
Edgerton, V. et al., "Training Locomotor Networks," Brain Research Reviews, vol. 57, No. 1, Jan. 2008, Published Online Sep. 16, 2007, 25 pages.
Kwakkel, G. et al., "Effects of Robot-assisted therapy on upper limb recovery after stroke: A Systematic Review," Neruorehabilitation and Neural Repair, vol. 22, No. 2, Mar. 2008, Published Online Sep. 17, 2007, 17 pages.
Courtine, G. et al., "Recovery of supraspinal control of stepping via indirect propriospinal relay connections after spinal cord injury," Nature Medicine, vol. 14, No. 1, Jan. 6, 2008, 6 pages.
Cowley, K. et al., "Propriospinal neurons are sufficient for bulbospinal transmission of the locomotor command signal in the neonatal rat spinal cord," The Journal of Physiology, vol. 586, No. 6, Mar. 15, 2008, Published Online Jan. 31, 2008, 13 pages.
Vallery, H. et al., "Compliant Actuation of Rehabilitation Robots," IEEE Robotics & Automation Magazine, vol. 15, No. 3, Sep. 12, 2008, 10 pages.
Edgerton, V. et al., "Robotic Training and Spinal Cord Plasticity," Brain Research Bulletin, vol. 78, No. 1, Jan. 15, 2009, Published Online Nov. 14, 2008, 19 pages.
Fuentes, R. et al., "Spinal Cord Stimulation Restores Locomotion in Animal Models of Parkinson's Disease," Science, vol. 323, No. 5921, Mar. 20, 2009, 14 pages.
Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Nov. 2009, Published Online Jul. 24, 2009, 5 pages.
Alto, L. et al., "Chemotropic Guidance Facilitates Axonal Regeneration and Synapse Formation after Spinal Cord Injury," Nature Neuroscience, vol. 12, No. 9, Sep. 2009, Published Online Aug. 2, 2009, 22 pages.
Hagglund, M. et al., "Activation of groups of excitatory neurons in the mammalian spinal cord or hindbrain evokes locomotion," Nature Neuroscience, vol. 13, No. 2, Feb. 2010, Published Online Jan. 17, 2010, 8 pages.
Wessels, M. et al., "Body Weight-Supported Gait Training for Restoration of Walking in People With an Incomplete Spinal Cord Injury: A Systematic Review," Journal of Rehabilitation Medicine, vol. 42, No. 6, Jun. 2010, 7 pages.
Zorner, B. et al., "Profiling locomotor recovery: comprehensive quantification of impairments after CNS damage in rodents," Nature Methods, vol. 7, No. 9, Sep. 2010, Published Online Aug. 15, 2010, 11 pages.
Ada, L. et al., "Mechanically assisted walking with body weight support results in more independent walking than assisted overground walking in non-ambulatory patients early after stroke: a systematic review," Journal of Physiotherapy, vol. 56, No. 3, Sep. 2010, 9 pages.
Duschau-Wicke, A. et al., "Patient-cooperative control increases active participation of individuals with SCI during robot-aided gait training," Journal of NeuroEngineering and Rehabilitation, vol. 7, No. 43, Sep. 10, 2010, 13 pages.
Rosenzweig, E. et al., "Extensive Spontaneous Plasticity of Corticospinal Projections After Primate Spinal Cord Injury," Nature Neuroscience, vol. 13, No. 12, Dec. 2010, Published Online Nov. 14, 2010, 19 pages.
Hidler, J. et al., "ZeroG: Overground gait and balance training system," Journal of Rehabilitation Research & Development, vol. 48, No. 4, Available as Early as Jan. 1, 2011, 12 pages.
Musselman, K. et al., "Spinal Cord Injury Functional Ambulation Profile: A New Measure of Walking Ability," Neurorehabilitation and Neural Repair, vol. 25, No. 3, Mar. 2011, Published Online Feb. 25, 2011, 9 pages.
Badia, J. et al., "Comparative analysis of transverse intrafascicular multichannel, longitudinal intrafascicular and multipolar cuff electrodes for the selective stimulation of nerve fascicles," Journal of Neural Engineering, vol. 8, No. 3, Jun. 2011, Published Online May 11, 2011, 13 pages.
Harkema, S. et al., "Effect of Epidural stimulation of the lumbosacral spinal cord on voluntary movement, standing, and assisted stepping after motor complete paraplegia: a case study," The Lancet, vol. 377, No. 9781, Jun. 4, 2011, Published Online May 20, 2011, 17 pages.
Wirz, M. et al., "Effectiveness of automated locomotor training in patients with acute incomplete spinal cord injury: A randomized controlled multicenter trial," BMC Neurology, vol. 11, No. 60, May 27, 2011, 5 pages.
Musienko, P. et al., "Controlling specific locomotor behaviors through multidimensional monoaminergic modulation of spinal circuitries," The Journal of Neuroscience, vol. 31, No. 25, Jun. 22, 2011, 32 pages.
Musienko, P. et al. "Multi-system neurorehabilitative strategies to restore motor functions following severe spinal cord injury," Experimental Neurology, vol. 235, No. 1, May 2012, Published Online Sep. 7, 2011, 10 pages.
Sun, F. et al., "Sustained axon regeneration induced by co-deletion of PTEN and SOCS3," Nature, vol. 480, No. 7377, Dec. 15, 2011, Published Online Nov. 6, 2011, 12 pages.
European Patent Office, Extended European Search Report Issued in Application No. 17163191.4, dated Oct. 9, 2017, Germany, 9 pages.

* cited by examiner

NEUROSTIMULATION SYSTEM FOR CENTRAL NERVOUS STIMULATION (CNS) AND PERIPHERAL NERVOUS STIMULATION (PNS)

CROSS REFERENCE TO RELATED APPLICATION

The present application claims priority to European Patent Application 17163191.4 entitled "A NEUROSTIMULATION SYSTEM FOR CENTRAL NERVOUS STIMULATION (CNS) AND PERIPHERAL NERVOUS STIMULATION (PNS)," filed on Mar. 28, 2017, the entire contents of which is incorporated herein by reference in its entirety for all purposes.

TECHNICAL FIELD

The present disclosure relates to an active closed-loop medical system, such as an active closed-loop medical system for neurostimulation, in the field of improving recovery after neurological disorders like spinal cord injury (SCI), for example after trauma.

BACKGROUND AND SUMMARY

EP 2 868 343 A1 discloses a system to deliver adaptive electrical spinal cord stimulation to facilitate and restore locomotion after neuromotor impairment. Inter alia, a closed-loop system for real-time control of epidural electrical stimulation is disclosed, comprising means for applying to a subject neuromodulation with adjustable stimulation parameters, the means being operatively connected with a real-time monitoring component comprising sensors continuously acquiring feedback signals from subject, signals providing features of motion of a subject, the system being operatively connected with a signal processing device receiving feedback signals and operating real-time automatic control algorithms, the signal processing device being operatively connected with the means and providing the means with new stimulation parameters, with minimum delay. This known system improves consistency of walking in a subject with a neuromotor impairment. A Real Time Automatic Control Algorithm is used, comprising a feed-forward component employing a single input-single output model (SISO), or a multiple input-single output (MISO) model. Reference is also made to Wenger et al., Closed-loop neuromodulation of spinal sensorimotor circuits controls refined locomotion after complete spinal cord injury, in Science Translational Medicine, vol. 6, num. 255, 2014.

WO 2002/034331 A2 discloses a non-closed loop implantable medical device system that includes an implantable medical device, along with a transceiver device that exchanges data with the patient, between the patient and the implantable medical device, and between a remote location and the implantable medical device. A communication device coupled to the transceiver device exchanges data with the transceiver device, the implantable medical device through the receiver device, and between the transceiver device and the remote location to enable bi-directional data transfer between the patient, the implantable medical device, the transceiver device, and the remote location. A converter unit converts transmission of the data from a first telemetry format to a second telemetry format, and a user interface enables information to be exchanged between the transceiver device and the patient, between the implantable medical device and the patient through the transceiver device, and between the patient and the remote location through the transceiver device.

US 2002/0052539 A1 describes a partial closed loop, non-continuous and non-real-time emergency medical information communication system and corresponding methods. The system permits an emergency alert to be issued on the basis of information sensed or processed by an implantable medical device (IMD) implanted within a body of a patient. The IMD is capable of bidirectional communication with a communication module, a mobile telephone and/or a Personal Data Assistant (PDA) located outside the patient's body. The communication module, a mobile telephone or a PDA is capable of communicating an emergency alert generated by the IMD to a remote computer via a communication system. At the remote computer system it may be determined that emergency remedial action is required. If so, the action is executed remotely from the remote computer system in the IMD via the communication system.

U.S. Pat. No. 7,149,773 B2 relates to description of methods, devices and systems for automatically generating invoices when medical services are provided to a patient. Invoices are automatically generated by the system, for example, when monitoring of certain aspects of the performance of an implantable medical device (IMD) implanted within a body of a patient is initiated by the patient or remotely, or when the delivery of a therapy to the patient through the IMD is initiated locally or remotely. The IMD is capable of bi-directional communication with a communication module, a mobile telephone and/or a Personal Data Assistant (PDA) located outside the patient's body. The system invoicing system may comprise the IMD, the communication module and/or a mobile telephone and/or a PDA, means for generating an invoice, a remote computer system, and a communication system capable of bi-directional communication, where the communication module, the mobile telephone and/or the PDA is capable of receiving information from the IMD or relaying information thereto.

U.S. Pat. No. 6,878,112 B2 discloses a plurality of co-operative and complementary software programs that are implemented in a web-enabled high speed computer system to remotely monitor, manage and modify the operational and functional parameters of a plurality of implanted medical devices (IMDs). The system utilizes virtual electrophysiologist module (VEM), chronic monitoring module (CMM) and prescription program module (PPM) programs to effect specific therapeutic and diagnostic methods for managing the IMDs, remotely on a condition and real-time basis. The modules enable remote and continuous monitoring, management and maintenance of the IMDs by identifying critical medical events, determining optimal clinical settings and upgrading performance parameters based on prescriptive data. The modules are implemented in a data center having high-speed computers operating in a web-enabled environment. The modules and the IMDs communicate through wireless communications system via a programmer or an interface medical unit (IMD).

EP 2 652 676 A1 relates to a gesture controlling for monitoring vital body signs and reuses an accelerometer, or, more precise, sensed accelerations of a body sensor for user control of the body sensor. This is achieved by detecting predefined patterns in the acceleration signals that are unrelated to other movements of the patient. These include tapping on/with the sensor, shaking, and turning the sensor. New procedures are described that make it possible to re-use the acceleration sensing for reliable gesture detection without introducing many false positives due to non-gesture movements like respiration, heart beat, walking, etc. Similar solutions for tapping detection of a user are known from U.S. Pat. Nos. 8,326,569 and 7,742,037.

Known stimulation systems use either Central Nervous System (CNS) stimulation, for example Epidural Electrical Stimulation (EES), or Peripheral Nerve System (PNS) Stimulation, for example Functional Electrical Stimulation (FES).

Epidural Electrical Stimulation (EES) is known to restore motor control in animal and human models and has more particularly been shown to restore locomotion after spinal cord injury by artificially activating the neural networks responsible for locomotion below the spinal cord lesion (Capogrosso, M, et al., A Computational Model for Epidural Electrical Stimulation of Spinal Sensorimotor Circuits, Journal of Neuroscience 4 Dec. 2013, 33 (49) 19326-19340, Courtine et al., Transformation of nonfunctional spinal circuits into functional states after the loss of brain input, Nat Neurosci. 2009 October; 12(10): 1333-1342, Moraud et al, Mechanisms Underlying the Neuromodulation of Spinal Circuits for Correcting Gait and Balance Deficits after Spinal Cord Injury, Neuron Volume 89, Issue 4, p 814-828, 17 Feb. 2016). EES does not directly stimulate motor-neurons but the afferent sensory neurons prior to entering into the spinal cord. In this way, the spinal networks responsible for locomotion are recruited indirectly via those afferents, restoring globally the locomotion movement by activating the required muscle synergies. The produced movement is functional; however, due to relatively poor selectivity (network activation instead of selective targeting of key muscles) the controllability is low and the imprecisions hinder fluidity and full functionality in the potential space of the movement.

Peripheral Nerve Stimulation (PNS) systems used to date in the clinic are known as Functional Electrical Stimulation (FES) that provides electrical stimulation to target muscles, either by directly stimulating muscles with surface electrodes, or by transcutaneous stimulation of the peripheral nerves. The resulting muscle fatigue has rendered FES unsuitable for use in daily life. Furthermore, successes have remained limited through cumbersome setups when using surface muscle stimulation, unmet needs in terms of selectivity (when using transcutaneous nerve stimulation) and a lack of stability (for example it may not be possible to reproduce exact electrode placement on a daily basis when stimulating muscles, moving electrodes due to clothes, sweating, etc.).

It is an object of the present disclosure to improve a neurostimulation system, e.g. in the field of improving recovery after neurological disorders like spinal cord injury (SCI), such as that which may occur after trauma, in that neuromodulation and/or neurostimulation may be provided in a more tailor-made manner, may be adapted to the patient's needs and may provide desired assistance in training and daily life for the patient, and which may be further adjusted to the progress of the rehabilitation of the patient.

This object is solved according to the present disclosure by a neuromodulation and/or neurostimulation system. Accordingly, a neuromodulation and/or neurostimulation system is provided comprising at least the following components:
at least one sensing unit,
at least control unit,
at least one stimulation unit,
at least one Central Nervous System (CNS) stimulation module for providing CNS stimulation,
at least one Peripheral Nervous System (PNS) stimulation module for providing PNS stimulation, and wherein at least one of the components of the neuromodulation and/or neurostimulation system is implantable.

The present disclosure is based on the basic idea that it may be possible to provide neuromodulation and/or neurostimulation with the above-described system to the Central Nervous System (CNS) and to the Peripheral Nervous System (PNS). Both the CNS and PNS may be stimulated at the same time or also intermittently or on demand. These two complementary stimulation paradigms may be combined into one strategy and made available for a patient being equipped with the system. For example, neuromodulation and/or neurostimulation of the CNS may be used to enhance and/or restore the capabilities of the patient as regards to movement, for example in a way that the existing ways of physiological signal transfer in the patient's body is supported such that the command signals for body movement or the like still are provided by the patient's nervous system, and supported and/or enhanced or translated by the CNS stimulation module. The stimulation provided by the PNS module may be used to locally steer and direct stimulation signals to specific peripheral nervous structures in order to trigger a specific movement and/or refine existing movements. Such a PNS stimulation may be used to refine and/or complete motion and/or movement capabilities of the patient being equipped with the system. It can, for example, be used to complete flexion or extension, lifting, turning or the like of including but not limited to toes, fingers, arms, feet, legs or any extremities of the patient. This may, for example, be done in cases where it is realized that the neuromodulation and/or neurostimulation provided by the CNS stimulation module is not sufficient to complete a movement or intended status of the patient. Then, such a movement or intended status may be completed or supported by stimulation provided by the PNS stimulation system. The PNS stimulation may be also used to reduce side effects or compensate for imprecisions of the CNS stimulation.

By way of such a combination of CNS stimulation and PNS stimulation a tailor-made stimulation and treatment of the patient may be provided.

The system may be completely implanted, partially implanted or more or less only provided by non-invasive components.

The system may be used as treatment related but not limited to restoring and/or training of the movements of the patient, locomotion, standing and/or walking, reaching and/or grasping, cardiovascular signals of the patient like blood pressure and/or blood pulse, tonus, nerve stimulation (e.g. nervous vagus stimulation), enhancement of the immunological system of the patient, body temperature and the like. Moreover, the general feeling and well-being (e.g. pain treatment) of the patient may be enhanced.

The Central Nervous System (CNS) stimulation module may be or may comprise an epidural stimulation module capable to provide epidural stimulation and/or a subdural stimulation module capable to provide subdural stimulation and/or an intracortical stimulation module capable to provide intracortical stimulation and/or an intraspinal stimulation module capable to provide intraspinal stimulation.

In particular, it may be possible that the epidural stimulation module is an Epidural Electrical Stimulation (EES) neurostimulation element.

EES does not directly stimulate motor-neurons but the afferent sensory neurons prior to entering into the spinal cord. In this way, the spinal networks responsible for locomotion are recruited indirectly via those afferents, restoring globally the locomotion movement by activating the required muscle synergies. The produced movement is functional; however, due to relatively poor selectivity (network activation instead of selective targeting of key muscles) the controllability is low and the imprecisions hinder fluidity and full functionality in the potential space of the movement.

In the context of locomotion, EES may additionally be used to further improve immediate and training-induced effects which may be further improved when proprioceptive afferent nerves are stimulated more selectively and aligned with the different phases of the gait cycle. During walking, these phases consist of an alternation between stimulation of the extension and flexion muscles of the right versus the left leg. Time-space EES may be used to restore both the swing phase (flexion) and the weight-bearing stance phase (extension) whereas continuous EES may block the limbs.

In particular, the epidural stimulation module (Epidural Electrical Stimulation (EES) neurostimulation element) may be arranged and configured as a spatially selective spinal implant, configured to work on the basis of temporally precise stimulation algorithms adjusted in a 'closed-loop' way using real-time motion feedback inputs as a part of the active closed-loop medical system.

The Peripheral Nervous System (PNS) stimulation module may be a Functional Electrical Stimulation (FES) module capable to provide Functional Electrical Stimulation (FES) and electrical stimulation of the peripheral nerves and thereby enhance selective refinement over the produced movements.

During Peripheral Nervous System (PNS) Stimulation, efferent motor-neuron axons and consequently muscles are stimulated directly and distally from the complex circuits in the spinal cord. Different types of interfaces with the periphery exist (X. Navarro, et al., A critical review of interfaces with the peripheral nervous system for the control of neuroprostheses and hybrid bionic systems, J. Peripher. Nerv. Syst. 10 (3) (2005) 229-258) and vary in terms of invasiveness, selectivity, and reliability; intra-neural implants are the most appropriate implants since they provide superior selectivity of stimulation, increased signal-to-noise ratio of recordings, and lower threshold of activation than extra-neural or epimysial implants (K. Yoshida, K. Jovanović, R. B. Stein, Intrafascicular electrodes for stimulation and recording from mudpuppy spinal roots, J. Neurosci. methods 96 (1) (2000) 47-55; J. Badia, et al., Comparative analysis of transverse intrafascicular multichannel, longitudinal intrafascicular and multipolar cuff electrodes for the selective stimulation of nerve fascicles, J. neural Eng. 8 (3) (2011) 036023).

Stimulating the peripheral nerves with intra-neural electrodes provides a local control that may be immediate and precise. However, the artificial stimulation is fatiguing to the muscles rapidly through an unnatural recruitment order of neurons. In fact, large diameter neurons and hence large diameter muscle fibers are recruited first using artificial electrical stimulation while spinal cord stimulation recruits afferent fibers before they enter the network within the spinal cord, thereby potentiating their natural recruitment of motor neurons (small diameter neurons first). On the contrary, while providing extremely precise and local control, PNS stimulation results in the excitation of a fiber type with rapid fatigue for ordinary tasks, being an important limitation to using it functionally.

Intra-neural peripheral nerve stimulation thus addresses needs in terms of increased selectivity, stability, and a reduction in cumbersomeness as such a system may be implemented with a single nerve implant. Thanks to the architecture of the peripheral nervous system, it allows to target multiple agonist and antagonist muscles by proximally interfacing the intra-neural fascicles with multiple channels, thus selectively stimulating the fibers that innervate the more distal muscles. These types of implants are well anchored within the nerve, thus conferring stability.

Intra-neural PNS stimulation targets directly specific muscles and can produce selective and controllable activations that allow expanding the reachable space of movements. However, it directly recruits motor axons and equally produces enhanced muscle fatigue when compared to spinal cord stimulation, and thus may not be sufficiently efficient for producing strong and coherent movements at any time. Additionally, the extreme selectivity that arises from the direct projections from the nerve to the muscle it innervates impede the generation of functional and weight-bearing movements. In fact, functional and multi-joint movements require the recruitment of muscles that are innervated by more than one nerve, and stimulating one nerve may not suffice to generate a usable movement.

As such, the combination of both stimulation types of CNS (e.g. EES), and PNS (e.g. FES), leverages the advantages of each stimulation paradigm and may restore functional, complex and fine movements after paralysis. Targeting the central and peripheral nervous system is complementary and may permit the restoration of functional and weight bearing movements.

Intra-neural peripheral nerve stimulation may certainly meet a number of the above mentioned needs in terms of increased selectivity, stability, and a reduction in cumbersomeness as such a system may be implemented with a single nerve implant. Thanks to the architecture of the peripheral nervous system, it allows to target multiple agonist and antagonist muscles by proximally interfacing the intra-neural fascicles with multiple channels, thus selectively stimulating the fibers that innervate the more distal muscles. These types of implant are well anchored within the nerve, thus conferring selectivity and stability. However, the direct recruitment of motor axons equally produces enhanced muscle fatigue when compared to muscle stimulation, and may thus not be efficient enough for producing strong and coherent movements at any time.

The more recently discovered indirect EES method builds on a strong scientific foundation and has the potential to overcome most of the inherent limitations to FES, but is lacking larger clinical experience so far.

The Central Nervous System (CNS) stimulation module may be at least partially implantable or at least partially implanted. By this, the CNS stimulation module may be placed close to the side, where the stimulation is needed. A very effective treatment with the system may then be provided to the patient.

The Peripheral Nervous System (PNS) stimulation module may be at least partially implantable or at least partially implanted. Generally speaking, it may also be possible that the PNS stimulation module may be not implanted, but only attached to the skin of the patient in a suitable manner. Nevertheless, by implanting the PNS stimulation module, the stimulation module may be placed close to the structures of interest, where the stimulation shall be provided. Also, more selective stimulation may be done with an implanted PNS stimulation module.

The components of the neuromodulation and/or neurostimulation system may for example form a closed-loop system.

The closed-loop system may be formed such that the control unit may receive input from the sensing unit. Such input, may be, for example, related to physiological signal(s)

like physiological electrical signals from a patient (i.e. the patient being equipped with the neuromodulation and/or neurostimulation system). By using the physiological feedback provided by the patient that is stimulated by the system, the stimulation may be better adapted to the needs of the patient. Such physiological signals may be related but not limited to physiological signals related to the gait cycle of the patient, locomotion, standing and/or walking, cardiovascular signals of the patient like blood pressure and/or blood pulse, tonus, nerve stimulation (e.g. nervous vagus stimulation), signals related directly or indirectly to the immunological system of the patient, body temperature and the like. Based on the signal or the signals the controller may control the stimulation unit and by this the CNS stimulation module and the PNS stimulation module. The CNS stimulation module and the PNS stimulation module may provide the required or desired neuromodulation and/or neurostimulation signals. These signals and the physiological response of the patient may be sensed by the sensing unit and the respective sensor signals can then be used as further basis for the control provided by the controlling unit. By this, a closed-system may be provided.

It may also be possible that components of the neuromodulation and/or neurostimulation system form an open-loop system. In such an example, the system and the electronic components utilized may be less sophisticated and thus a less expensive system may be provided. Also, the system complexity may be reduced, which might also increase reliability of the system with less efforts. In particular, for an open-loop system, a predetermined stimulation protocol and setup may be provided to the patient. If changes are desired, such changes may be introduced into the system by means of an update or the installation of an additional stimulation routine. Thus, a very simple system layout may be achieved by the open-loop approach.

Furthermore, the control unit may be configured such that control may be done in real-time. In particular, real-time may be understood in a way that the delay between sense signals and provided stimulation signals shall be not more than 30 ms, as also already mentioned in WO 2016/0279418 A1.

Real-time control in terms of the present disclosure and its preferred embodiments, (e.g. that the delay of between sense signals and provided stimulation signals shall be not more than 30 ms), may be beneficial for the open-loop approach and also for closed-loop approach. It may be very helpful for the patient equipped with the system to have stimulation at the moment or close to the moment needed to proceed, for example, with the desired movement.

Furthermore, it may be possible that the Peripheral Nervous System (PNS) stimulation module may comprise at least one electrode having at least one fixation element for anchoring the electrode in or to surrounding structures. By this it may be possible to keep the position of the electrode of the PNS stimulation module close to the structure which shall receive the stimulation or shall be stimulated by means of the PNS stimulation module.

Moreover, the control unit may be configured such that based on the sensing signals provided and gained by means of the sensing unit, the PNS stimulation provided by the PNS stimulation module and/or CNS stimulation provided by the CNS stimulation module may be adjusted and/or adapted to at least partially match stimulation control signals provided by the control unit to control the PNS stimulation module and/or the CNS stimulation module with physiological signals related to a move intention of a subject decoded from its brain and/or nervous system, and/or at least partially match the stimulation control signals provided by the control unit to control the PNS stimulation module and/or the CNS stimulation module with a desired kinematic trajectory, and/or at least partially match the stimulation control signals provided by the control unit to control the PNS stimulation module and/or the CNS stimulation module with desired forces with respect to a surface, on which the subject is located or that the subject is touching, and/or at least partially match the stimulation control signals provided by the control unit to control the PNS stimulation module and/or the CNS stimulation module with muscle activation for certain gait patterns and/or grasp types and/or movements.

By at least partially matching stimulation control signals, a specific neuromodulation or stimulation may be provided. Furthermore, by detecting physiological signals related to a move intention of the subject, which may be decoded from the brain and/or the nervous system, accurate neuromodulation and triggering sense for the neuromodulation or neurostimulation may be obtained and an accurate neuromodulation or neurostimulation may be provided by the system. By at least partially matching the stimulation control signals in connection with the desired kinematic trajectory, a correction of unwanted signals may be done and the intended move may be supported in a tailor-made manner. Additionally, it may be possible to at least partially match the stimulation control signals to control the PNS stimulation module and/or the CNS stimulation module with the intended forces and needed forces that shall be touched by the subject. Such support may be connected to standing and walking or control of the movement of the hands or arms of the patient. There may be also a matching of the stimulation control signals with physiological signals in order to detect and activate and control muscle activation for certain gait patterns and/or grasp types and/or movements. By finding out the specific triggering physiological signals for such gate patterns or grasp types and movements, specific support by means of neuromodulation and/or neurostimulation may be provided by the system.

Furthermore, it may be possible that the control unit may be configured such that signals provided by the sensing unit and related to the movement of the subject may be decoded, for example continuous movement of the subject and/or signals related to force(s) and/or EMG activity and/or kinematic trajectories may be decoded. There may be an interaction of the stimulation in connection with the physiological signals of the subject. This interaction of stimulation and the physiological signals may be used to tailor the neuromodulation or neurostimulation provided by the system. In particular, tonic or phasic stimulation may be provided by the CNS stimulation module and there may also be a phasic stimulation on the PNS neurostimulation module, which may be triggered by a triggering event. Such a triggering event may be provided by the sensing unit, which may make use of EEG or EMG or force signals or cortical signals or from voice control or movement signals or the like. Here, external sensors like accelerometers, force sensors, interactive sensors or even a microphone for voice control may be used. Also, cameras or the like may be used to provide the respective signals. Further, for at least partially matching the stimulation control signals there may be an interaction of the stimulation and the triggering event may be a specific movement or a force or an EMG profile, the CNS and PNS stimulation may be tonic, phasic or triggered by any other signal.

The control unit may be configured such that the stimulation provided by the PNS stimulation module and the stimulation provided by the CNS stimulation module are at least partially interleaved. By this specific stimulation, the motor output of the patient may be supported.

Additionally, it may be possible that the control unit may be configured such that the PNS stimulation provided by the PNS stimulation module and CNS stimulation provided by the CNS stimulation module may be at least partially superimposed. By this, the effect of the simulation may be refined.

As such, it may also be possible that the control unit may be configured such that the PNS stimulation provided by the PNS stimulation module or the CNS stimulation provided by the CNS stimulation module is at least partially used for correction of the stimulation provided by the other (e.g. another) stimulation module to refine motor output. Such an approach may be used to support movements, correct the movement itself and specific movements and assist the patient within the movement.

The control unit may be capable to independently control and switch on and off either the PNS stimulation module or the CNS stimulation module. By this it may be possible to provide only CNS stimulation or PNS stimulation. Such a capability of the system may also increase the way in how the system may be used. Depending on the situation of the subject being equipped with the system, the stimulation may be adjusted to the specific needs.

Furthermore, the present disclosure relates to a method of providing neuromodulation and/or neurostimulation by providing Central Nervous System (CNS) stimulation combined with a Peripheral Nervous System (PNS) stimulation, by using a neuromodulation and/or neurostimulation system such as that described in detail above.

More specifically, the present disclosure relates to a method of providing neuromodulation and/or neurostimulation by providing Central Nervous System (CNS) stimulation combined with Peripheral Nervous System (PNS) stimulation, by using a neuromodulation and/or neuro stimulation system, the neuromodulation and/or neurostimulation system comprising at least the following components:

at least one sensing unit,
at least control unit,
at least one stimulation unit,
at least one Central Nervous System (CNS) stimulation module for providing CNS stimulation,
at least one Peripheral Nervous System (PNS) stimulation module for providing PNS stimulation; and
wherein at least one of the components of the neuromodulation and/or neurostimulation system is implantable or at least partially implantable.

In one example of such a method, the at least one CNS stimulation module is or comprises one or more of an epidural stimulation module capable to provide epidural stimulation, a subdural stimulation module capable to provide subdural stimulation, an intracortical stimulation module capable to provide intracortical stimulation, and/or an intraspinal stimulation module capable to provide intraspinal stimulation; and wherein the PNS stimulation module is a Functional Electrical Stimulation (FES) module capable to provide electrical stimulation of the peripheral nerves, the PNS stimulation module further comprising at least one electrode having at least one fixation element for anchoring the electrode in or to surrounding structures.

In another example of such a method, the control unit is configured such that based on sensing signals provided and gained by means of the sensing unit, the PNS stimulation provided by the PNS stimulation module and/or the CNS stimulation provided by CNS stimulation module can be adjusted and/or adapted to:

at least partially match stimulation control signals provided by the control unit to control the PNS stimulation module and/or the CNS stimulation module with physiological signals related to a move intention of a subject decoded from its brain and/or nervous system, and/or at least partially match the stimulation control signals provided by the control unit to control the PNS stimulation module and/or the CNS stimulation module with a desired kinematic trajectory, and/or at least partially match the stimulation control signals provided by the control unit to control the PNS stimulation module and/or the CNS stimulation module with desired forces with respect to a surface on which the subject is located or that the subject is touching, and/or at least partially match the stimulation control signals provided by the control unit to control the PNS stimulation module and/or the CNS stimulation module with muscle activation for certain gait patterns and/or grasp types and/or movements; and wherein the control unit is configured such that the sensing signals provided by the sensing unit can be decoded, the sensing signals related to movement of the subject, and wherein movement of the subject includes one or more of continuous movement of the subject, signals related to force(s), EMG activity, and/or kinematic trajectories.

In still another example of such a method, the control unit is configured such that the PNS stimulation provided by the PNS stimulation module and the CNS stimulation provided by the CNS stimulation module is at least partially interleaved or at least partially superimposed.

In still another example of such a method, the control unit is configured such that the PNS stimulation provided by the PNS stimulation module or the CNS stimulation provided by the CNS stimulation module is at least partially used for correction of stimulation provided by another stimulation module to refine motor output.

In still another example of such a method, the control unit is capable to independently control and switch on and off either the PNS stimulation module or the CNS stimulation module.

Furthermore, in connection with the present disclosure the use of a neuromodulation and/or neurostimulation system according to that described above for providing neuromodulation and/or neurostimulation by providing Central Nervous System (CNS) stimulation combined with Peripheral Nervous System (PNS) stimulation is disclosed.

In connection with the Peripheral Nervous System (PNS) stimulation, a stimulation of the upper limb nerves, i.e. the radial, ulnar and/or median nerves may be provided. Also, the lower limb nerves like the sciatic and/or femoral nerves may be provided in connection with PNS stimulation. All PNS stimulation may be done by targeting one of the above-mentioned nerves with intra-neural electrodes (transversal or longitudinal) or epi-neural (cuff) electrodes.

In connection with the Central Nervous System (CNS) stimulation the following nervous structures may be stimulated: for the upper limb movements the cervical spinal cord or hand/arm motor cortex may be stimulated with the CNS stimulation module. For the lower limb movements the lumbosacral spinal cord or the lower limb may be stimulated. All these nerves may be targeted with epidural, subdural or intra-spinal/intra-cortical stimulation.

The sensing module may sense muscle activity (by means of surface or intramuscular EMG electrodes, one or several electrodes to construct control signals). By means of variables like kinematic markers or IMU the kinematic activity of the patient may be sensed. Also there may be several sensors, which detect forces on the skin or forces intended to be provided by the subject by means of pressure sensors, for example in a foot insole or in a glove. Such sensors may be also wearables. Neural signals such as field potential, multi-unit, single spikes, etc, may be detected by EEG, ENG, ECoG, intra-cortical electrode arrays, patch-clamp electrodes, or single penetrating electrodes.

Both stimulation units may use a common implantable pulse generator (IPG), which may be used for providing the necessary stimulation current and signals for the CNS stimulation module and the PNS stimulation module. It may also be possible that two separated IPGs are provided, one for the PNS stimulation module and one for the CNS stimulation module.

The stimulation parameters for the Peripheral Nervous System (PNS) stimulation and the EES stimulation may be frequency, amplitude, pulse-width and the like.

A suitable frequency range is, for example, between approx. 30 Hz and 120 Hz.

The amplitude values can be chosen between 20 and 1000 uA.

The pulse-width values may be chosen between 0.040 and 1 msec. Preferred parameters are in a range of 50-300 uA for amplitude with 40-120 usec pulse width.

The above values for amplitude and pulse-width depend inter alia on the interface being used and the invasiveness it represents. For example, intraneural electrodes are more invasive than, for example, epineural CUFFs (and both could be used in the system), so they may utilize a lower amount of stimulus charge to recruit the axons. For those intraneural electrodes, this total charge injected per stimulation pulse (charge=amplitude×pulse width) may not be higher than 120 nC (limit of electrode itself rather than tissue—risk of delamination, etc.). Within this constraint, the amplitude may be between 20 and 1000 uA, the pulse-width between 0.040 and 1 msec. Preferred parameters are in a range of 50-300 uA for amplitude with 40-120 usec pulse width.

EES may be phasic or tonic, selective PNS is always phasic. Phasic is defined as locked to defined events in the sensing signals (decoded intention, continuous decoding, muscle activity onset, movement onset, event during defined movement (foot off or foot strike during gait for instance).

In connection with the closed-loop system the following way of working is done by the whole system:

Based on the sensing signals, the stimulation in PNS and/or CNS may be adjusted in real-time to
match intention decoded from the brain, and/or
continuously decode movement, force or EMG from signals, and/or
match pre-defined kinematic trajectory, and/or
match desired forces with respect to surface softness (of ground or grasped object), and/or
match muscle activation for certain gait patterns/grasp types.

BRIEF DESCRIPTION OF THE DRAWINGS

Further details and advantages of the present disclosure shall now be disclosed in connection with the drawings.

DETAILED DESCRIPTION OF DRAWINGS

Figure 1:
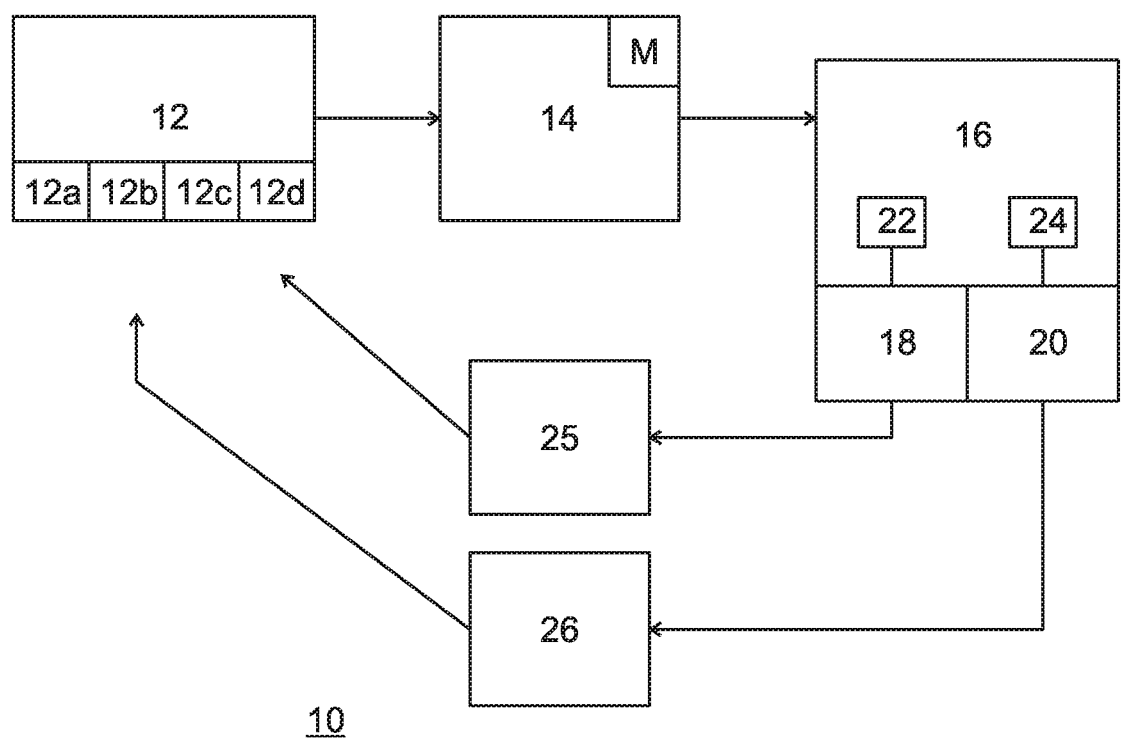
FIG. 1 shows a schematic view of the layout of an embodiment according to the present disclosure of the neuromodulation and/or neurostimulation system.

FIG. 1 shows in a schematical view the layout of the neuromodulation and/or neurostimulation system 10 according to the present disclosure.

The system 10 comprises the components sensing unit 12, control unit 14, stimulation unit 16, Central Nervous System (CNS) stimulation module 18 and a Peripheral Nervous System (PNS) stimulation module 20.

The stimulation unit 16 comprises one Implantable Pulse Generator (IPG) 22 for the CNS stimulation module 18 and another IPG 24 for the PNS stimulation module 20.

It is also possible that only one IPG for both the CNS stimulation module 18 and for the PNS stimulation module 20 is provided.

Figure 2:
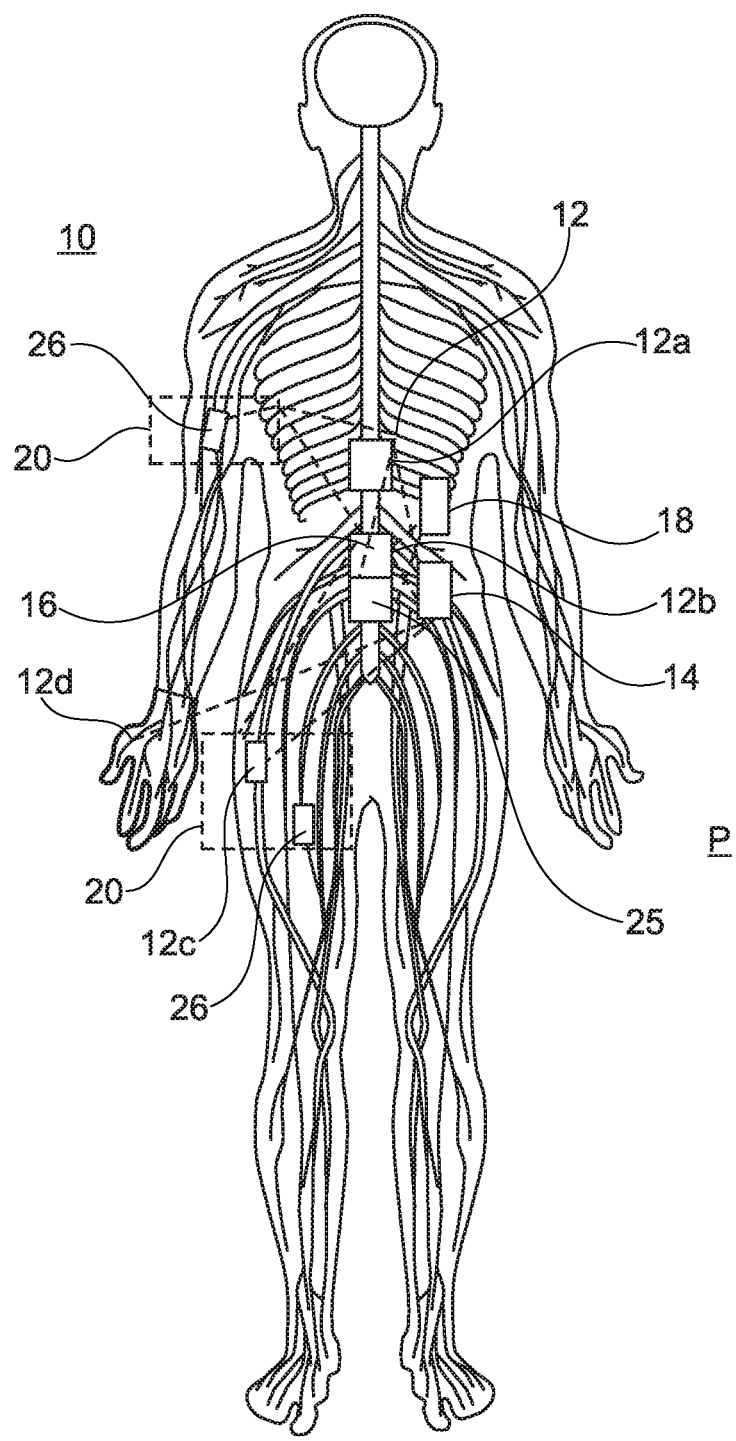
FIG. 2 shows a schematic view of the implanted system and the subject being equipped with the system.

The system 10 is at least partially implantable, but also comprises sensors, which are or are not implanted and connected either via wires to a connector and then to a recording chamber, or with a wireless data transmission link with the control unit 14 (see FIG. 2).

As can be seen in FIG. 2, there are sensing units 12a and 12b, which are implanted in the patient. These sensing units 12a, 12b are sensors to monitor and sense physiological signals, here sensing electrodes.

The control unit 14 is also implanted in the patient P. It is also possible that this control unit is not implanted.

The control unit 14 comprises at least one memory M.

This memory provides storage capacity for data, inter alia control instructions for performing the control of the system 10.

Such instructions include but are not limited to how to match stimulation control signals provided by the control unit 14 to control the PNS stimulation module 20 and/or the CNS stimulation module 18 with physiological signals related to a move intention of a subject decoded from its brain and/or nervous system, and/or to match the stimulation control signals provided by the control unit 14 to control the PNS stimulation module 20 and/or the CNS stimulation module 18 with a desired kinematic trajectory, and/or to match the stimulation control signals provided by the control unit 14 to control the PNS stimulation module 20 and/or the CNS stimulation module 18 with desired forces with respect to a surface, on which the subject is located or that the subject is touching, and/or to match the stimulation control signals provided by the control unit 14 to control the PNS stimulation module 20 and/or the CNS stimulation module 18 with muscle activation for certain gait patterns and/or grasp types and/or movements.

These instructions may be part of a control routine or control software or stored as separate software modules or stored into the memory as instruction data.

The link between sensor signals and the instructions may be realized by providing respective meta data, which are stored separately in the memory M, for example in a meta data memory part or storage.

The CNS stimulation module 18 and the PNS stimulation module 20 may also be implanted in the patient P.

Thus, also the respective IPGs 22 and 24 may be implanted in the patient P.

However, there may also be sensors 12*c* and 12*d*, which may not be implanted, but which may be attached to the skin of the patient P and provided as wearables. They may be attached to the skin of the patient P by gluing or worn as gloves (e.g. 12*c*) or the like.

The Central Nervous System stimulation module 18 is in the shown embodiment an epidural stimulation module capable to provide epidural stimulation via electrodes 25.

Generally, it may be also provided as a stimulation module that is capable to provide subdural stimulation or intra-cortical stimulation or intra-spinal stimulation.

The PNS stimulation module 20 may be a functional electrical stimulation module capable to provide electrical stimulation of the peripheral nerves (e.g. PNS stimulation) via electrodes 26.

As can be seen in FIG. 1 and FIG. 2, the PNS stimulation module 20 comprises electrodes 26.

The electrodes 26 may be implanted and may have fixation elements for anchoring the electrodes 26 in the surrounding structures at the implantation side.

The control unit 14 may receive signals from the various sensors of FIG. 1 and FIG. 2 and may employ the various actuators of FIG. 1 and FIG. 2 to adjust stimulation parameters based on the received signals and instructions stored on the memory of the control unit 14.

The control unit 14 may be configured such that based on the sensing signals provided and gained by means of the sensing unit 12, the stimulation provided by the PNS stimulation module 20 and/or provided by CNS stimulation module 18 may be adjusted and/or adapted to match the stimulation control signals provided by the control unit 14 to control the PNS stimulation module 20 and/or the CNS stimulation module 18 with physiological signals related to a move intention of a subject decoded from its brain and/or nervous system, and match the stimulation control signals provided by the control unit 14 to control the PNS stimulation module 20 and/or the CNS stimulation module 18 with a desired kinematic trajectory, and match the stimulation control signals provided by the control unit 14 to control the PNS stimulation module 20 and/or the CNS stimulation module 18 with desired forces with respect to a surface, on which the subject is located or that the subject is touching, and match the stimulation control signals provided by the control unit 14 to control the PNS stimulation module 20 and/or the CNS stimulation module 18 with muscle activation for certain gait patterns and/or grasp types and/or movements.

Furthermore, the control unit 14 may be configured such that signals provided by the sensing unit 12 and related to movement of the subject may be decoded, for example continuous movement of the subject and/or signals related to force(s) and/or EMG activity and/or kinematic trajectories may be decoded.

The system 10 may work as a closed-loop system in real-time.

In particular, the stimulation signals provided by the CNS stimulation module 18 and its electrodes 25 and by PNS stimulation module 20 and its electrodes 26 may be monitored and recorded together with the respective response of the patient by means of the sensing unit(s) and sensor(s) 12, 12*a*, 12*b*, 12*c*, 12*d*.

It is also possible in general that the system 10 is and may work as a open-loop system. In particular, it is possible that there might be pre-programmed sequences of stimulation sets or patterns to achieve a desired motor outcome.

In particular, the sensing signals may be used to influence the stimulation signals and the stimulation signals and the physiological response thereto is again sensed by the sensing unit 12 and again influences the control unit 14.

This way of working may be controlled by the control unit 14, which may be configured such that the control is done in real-time.

Real-time controlling and working of the system 10 means that the control is done with minimum delay, i.e. within a range of approx. 0 up to 30 ms.

The control unit 14 may be configured such that the PNS stimulation provided PNS stimulation module 20 and the CNS stimulation provided by the CNS stimulation module 18 is at least partially interleaved.

Also, the control unit 14 may be configured such that the PNS stimulation provided by the PNS stimulation module 20 and the CNS stimulation provided by CNS stimulation module 18 is at least partially superimposed.

By interleaving or superimposing the signals, it may be possible to stimulate in a tailor-made way.

Moreover, the control unit 14 may be configured such that the stimulation provided by either the PNS stimulation module 20 or the CNS stimulation module 18 is at least partially used for correction of the stimulation effect provided by the other stimulation module to refine motor output.

Furthermore, the control unit 14 may be capable to independently control and switch on and off either the PNS stimulation module 20 or the CNS stimulation module 18. In other words, the PNS stimulation module 20 and the CNS stimulation module 18 may be controlled independently from each other.

Such a control may be done by the control unit 14.

The function of the system 10 can be described as follows:

The system 10 provides a new electrical stimulation paradigm for the restoration or fine and controllable motor function that targets both the central and the peripheral nervous system in a refined neuroprosthetic system addressing neuromotor disorders. As described above, in combining electrical stimulation of the central nervous system (spinal cord) with intermittent electrical stimulation of the peripheral nerves in real-time instead of using either spinal cord stimulation or nerve stimulation alone, a specific and more general stimulation approach may be established.

It may be possible to exploit the complementary advantages of both stimulation types.

In unimpaired individuals, motor outputs are constantly refined and adjusted based on information from the periphery (for instance, proprioception, sensation, vision).

To achieve such a fine-tuning, stimulation paradigms may need to recruit specific muscles selectively to compensate for imprecisions in the motor output generated by central stimulation paradigms.

The system 10 may be able to use information from the peripheries and from the Central Nervous System in order to refine and adjust the desired stimulation output either by way of the CNS stimulation module 18 or the PNS stimulation module 20.

Thus, there may be a combination of electrical stimulation of the spinal cord and the peripheral nerves. The combination of both strategies may yield a highly refined and much more efficient neuroprosthetic rehabilitation of motor control, with potential applications in both the upper and lower limb paralysis framework.

In the framework of paralysis, spinal cord stimulation recruits functional networks below the lesion and activates muscle synergies that act as building blocks for functional movements. While the created movement may be strong as a result of the activation of the movement related muscle synergies, control and execution of fine movements may be a difficult task as the generated movement and its imprecisions may hinder fluidity and full functionality in the potential space of the movement.

Peripheral nerve stimulation may target directly specific muscles and may produce selective and controllable activations that may allow expanding the reachable space of movements. The bottleneck of this extreme selectivity that arises from the direct projections from the nerve to the muscle it innervates consists in the impossibility of generating functional and weight-bearing movements. In fact, functional and multi-joint movements require the recruitment of muscles that are innervated by more than one nerve, and stimulating one nerve may not suffice to generate a usable movement.

As such, the combination of both stimulation types may leverage the advantages of each stimulation paradigm and may restore functional, complex and fine movements after paralysis.

As shown in FIG. 3, FIG. 4, FIG. 5, and FIG. 6, the feasibility of the above paradigm has been demonstrated in a rat model of paralyzing spinal cord injury.

Figure 3:
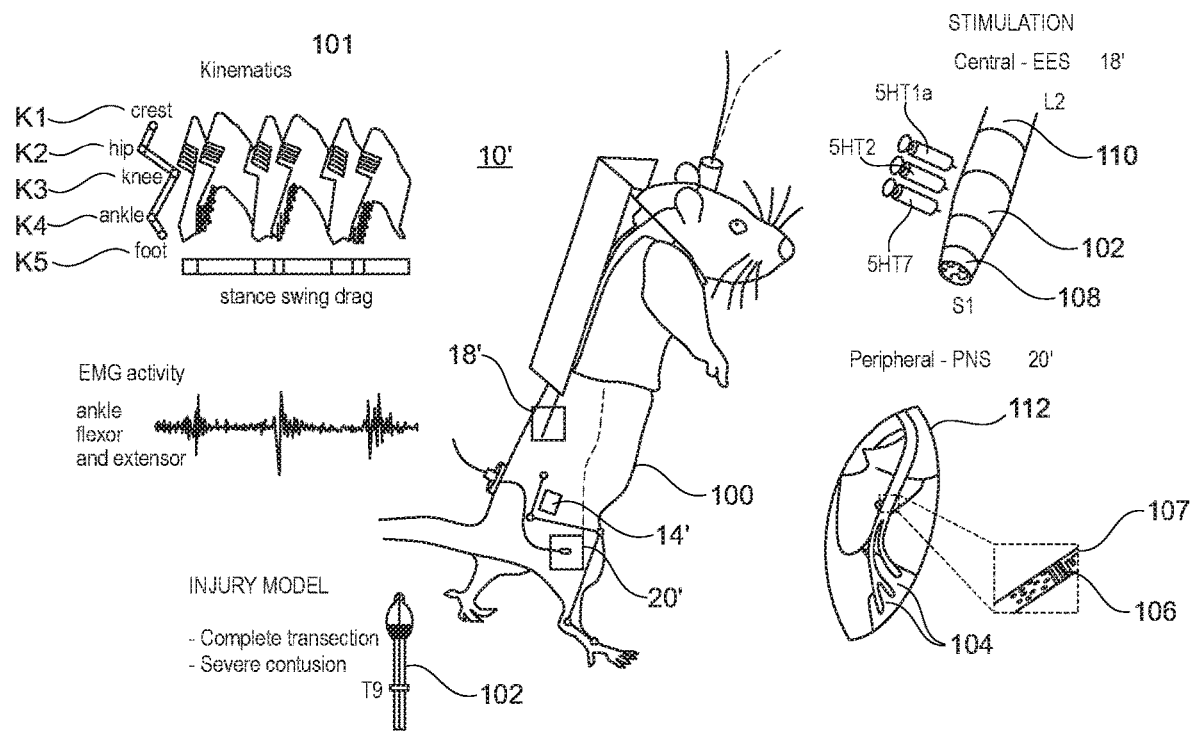
FIG. 3 shows a schematic overview about a feasibility study conducted with rats, showing an example of the system that targets lower limb movements according to the present disclosure.

FIG. 3 shows in a schematic view an example of an implementation of the system 10' in a feasibility study conducted with a rat 100 that aims at restoring refined locomotion after paralyzing spinal cord injury.

Similar implementation is possible in other mammals or human beings.

There is a CNS stimulation module 18' and a PNS stimulation module 20' having the structural and functional features as described above, but adjusted to the size of the rat 100.

In this example, the spinal cord 102 of the rat 100 is injured at the mid-thoracic level (approx. T8/T9) by either a severe spinal cord contusion or a complete spinal cord transection (cf. lower left part of FIG. 3).

EMG signals from ankle muscles 104 are recorded via bipolar wire electrodes 106 of a neural polyimide-based multi-channel implant 107 implanted within the muscles (cf. lower right and upper left part of FIG. 3).

Leg joint kinematics are recorded by means of a recording system 101 via reflective markers that are glued with double-sided tape to the joints. CNS stimulation is provided on the epidural lumbosacral spinal cord 102 via two monopolar wire electrodes 108, 110 placed on levels L2 and S1 respectively (cf. upper right part of FIG. 3).

5HT7, 5HT2 and 5HT1a represent pharmaceuticals that may be used to support the stimulation.

The recorded signals relate to kinematics (i.e. stance, swing and drag) of parts of lower extremity, here
the crest, i.e. kinematic crest signal K1,
the hip, i.e. kinematic hip signal K2,
the knee, i.e. kinematic knee signal K3,
the ankle, i.e. kinematic ankle signal K4, and
the foot, i.e. kinematic foot signal K5.

Furthermore, by means of the recording system 101 the EMG activity is recorded. Here the EMG signals related to ankle, flexor and extensor are recorded.

The signals recorded by means of the recording system 101 may be stored in a memory of the recording system 101. They may also be used by the control unit of the system 10' (not shown, but functionality is described above in connection with control unit 14).

PNS stimulation is provided via an intra-neural polyimide-based multi-channel implant that is inserted in the proximal sciatic nerve 112 (above the branching point into separate fascicles) (cf. lower right part of FIG. 3).

In this setup, the wires from the EMG electrodes and the epidural spinal cord electrodes are all routed subcutaneously to a common connector that is cemented with dental cement to the skull of the rat. The amplifier for EMG signals and stimulator providing the spinal cord may be plugged to this connector. The wires from the intra-neural electrode are routed subcutaneously to a plug on the lower back of the rat, to which the stimulator may be plugged.

As shown in the upper left part of FIG. 3, the kinematics (of crest, hip, knee, ankle and foot) and the respective EMG activity (for ankle, flexor and extensor) are recorded by the sensors of the system 10'.

Figure 4:
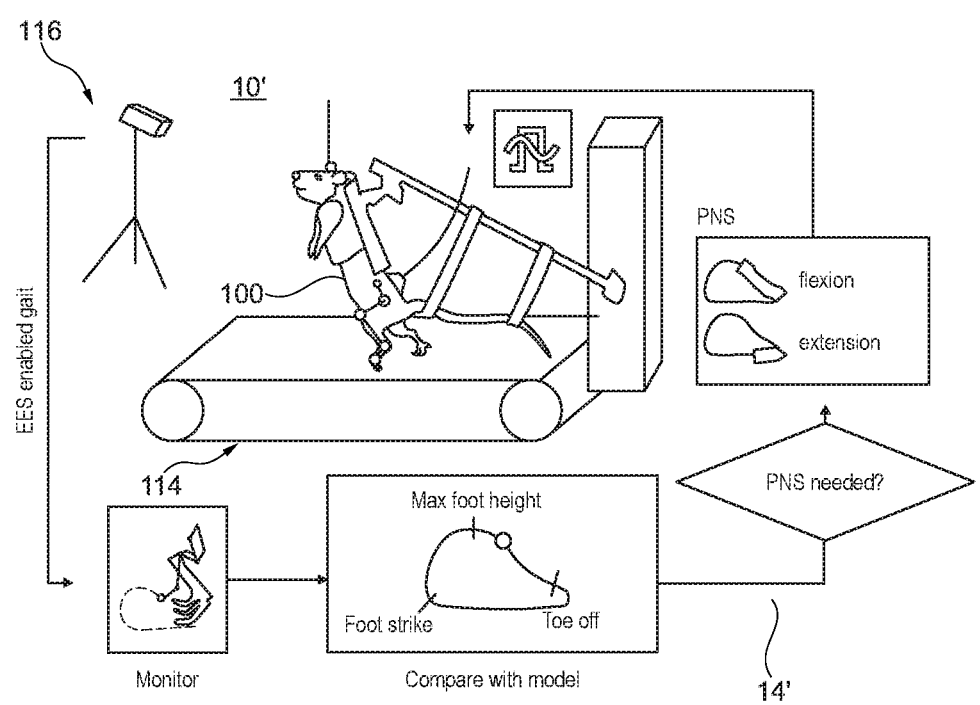
FIG. 4 shows a further schematic overview about a feasibility study conducted with rats, showing an example of how CNS and PNS stimulation may be used based on recorded sensing signals in the framework of restoring lower limb movement for the system and method according to the present disclosure.

FIG. 4 shows an example of how such a system 10' as presented in FIG. 3 may be used in real time to generate functional and refined movements.

Epidural electrodes, i.e. the two monopolar wire electrodes 108, 110 (cf. upper right part of FIG. 3 and CNS stimulation module 18') on the lumbosacral spinal cord 102 electrically stimulate the locomotor networks and produce functional gait patterns.

The produced movements of the rat 100 on a treadmill 114 are monitored in real time using reflective markers that are glued on the hind-limb joints (crest, hip, knee, ankle, foot-tip) inter alia by means of a camera 116.

In this example the control unit 14' (which can inter alia control wirelessly the components of the system 10') compares the produced gait patterns in real-time to a model gait cycle and recognizes main events and their timing such as foot strike, toe-off or maximal foot height in real time.

Also in this example, if the produced gait would not match the desired model gait cycle, selective PNS is used at defined phases during the gait cycle to refine the produced gait.

Bilateral intraneural electrodes in the right and left sciatic nerve deliver phasic electrical stimulation to correct for the noticed imprecisions in the patterns and refine the gait.

In this example, the intensity of the PNS is controlled with the frequency of the delivered pulses.

Figure 5:
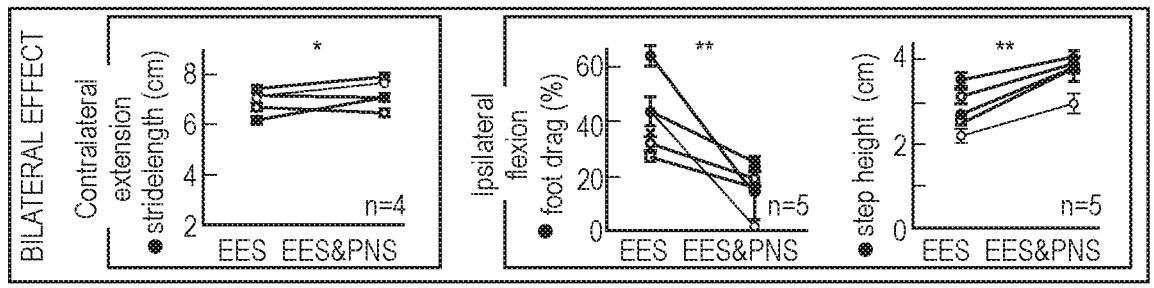
FIG. 5 shows a further schematic overview about a feasibility study conducted with rats, providing a proof of concept for the system and method according to the present disclosure.
Figure 5:
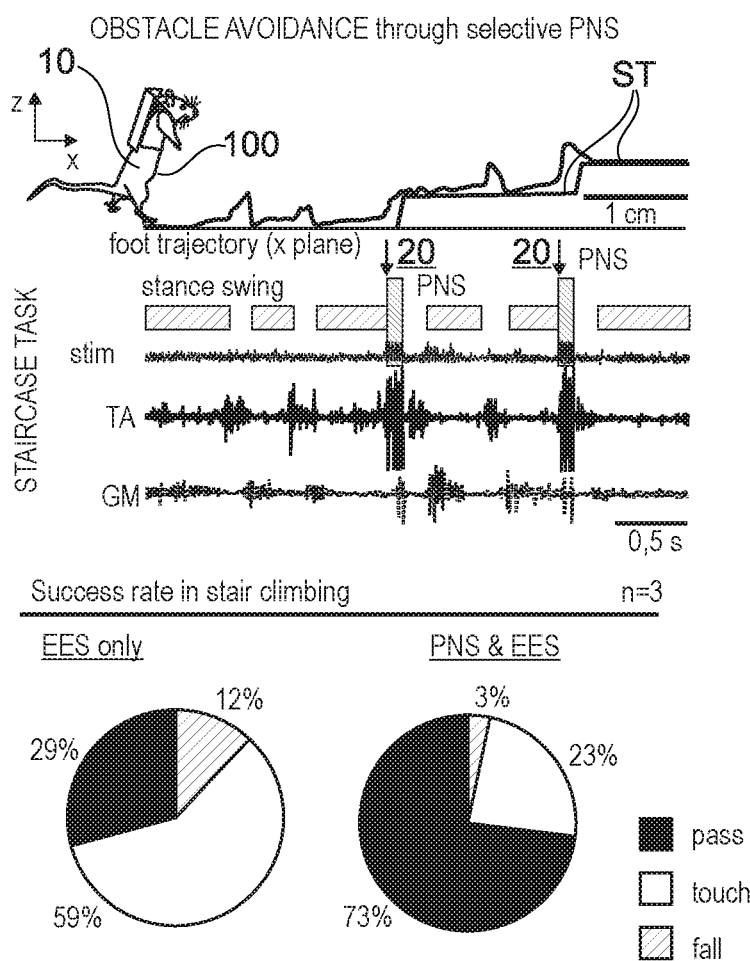

FIG. 5 (top) shows preliminary results that were obtained using the system described in FIGS. 3 and 4. Ankle flexion was enhanced through selective sciatic nerve stimulation of the peroneal fascicle at the beginning of the swing phase while ankle extension was enhanced through selective stimulation of the sciatic nerve tibial branch via different active sites at the end of stance phase.

Adding PNS to CNS had major effects on the leg being stimulated and on the contralateral leg. In fact, a significant increase was obtained in the step height of the leg that was additionally stimulated with PNS.

Additionally, the dragging of the foot that was stimulated additionally with PNS was significantly reduced when compared to CNS only.

Adding PNS by means of the Peripheral Nervous System (PNS) stimulation module 20 on one leg also had a significant effect on the other leg, for instance it increased the stride length of that leg considerably.

This refinement of the gait allowed the rats 100 to walk overground (FIG. 5 bottom) and climb on stairs (see middle section of FIG. 5 with stairs ST) with significantly reduced amount of failures and tumbling.

This present disclosure has enormous potential to restore fine movements in people affected by paralysis.

Especially in the case of upper limb paralysis, spinal cord stimulation has shown fairly limited success in being able to selectively activate forearm or finger muscles.

Activating the reaching and grasping synergies centrally and refining those peripherally has thus enormous potential for the restoration of functional, refined and controllable upper limb movements after paralysis.

Central neuromodulation, under the form of electrical stimulation of the spinal cord produces motor synergies resulting in functional movements but those movements are restricted in space. Stimulating the peripheral nerves additionally with different stimulation frequencies on top of the central neuromodulation allows
i) to gradually refine the produced movements and
ii) to locally expand the reachable space in a highly controllable way.

Figure 6:
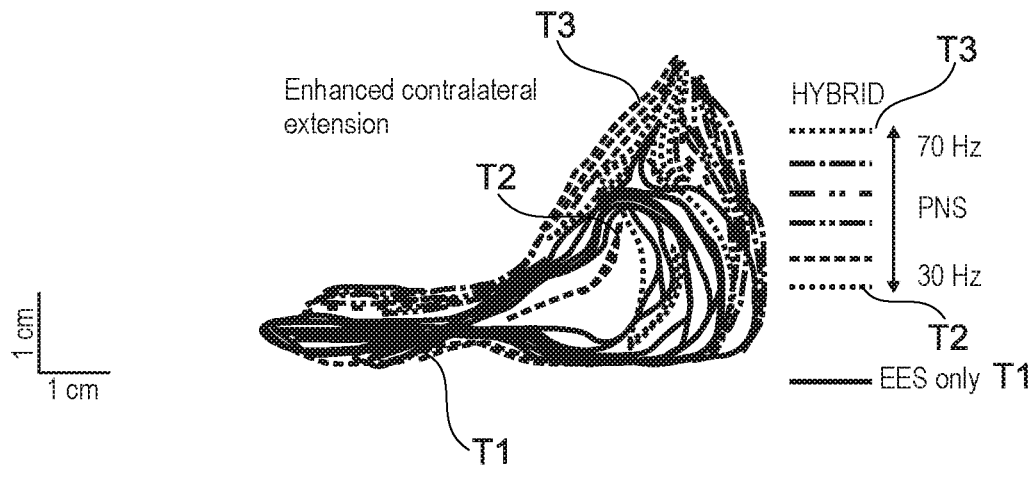
FIG. 6 shows a further illustration of gait patterns produced by CNS stimulation under the form of EES only and of gait patterns produced by a combined PNS and CNS stimulation, with PNS locally refining the produced patterns depending on the frequency of PNS stimulation that is employed, providing an illustration of the efficiency of the system for restoring refined lower limb movements according to the present disclosure.
Figure 6:
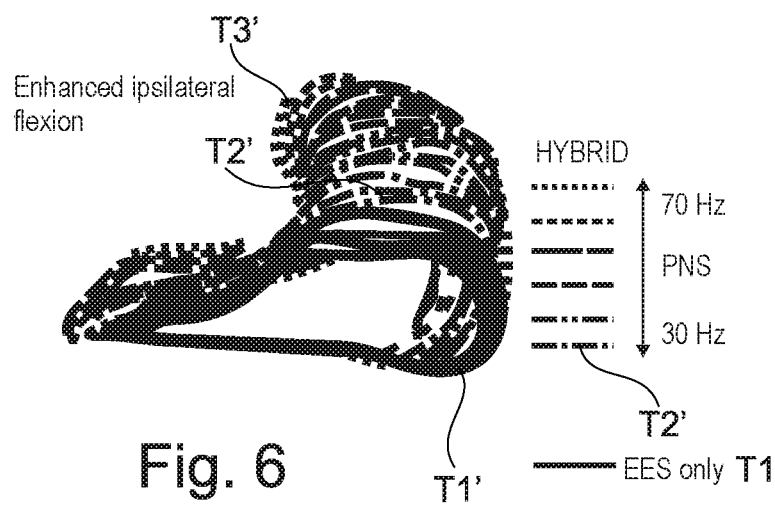

FIG. 6 illustrates this concept in the framework of lower limb paralysis.

Foot trajectories T1, T1' (black) are obtained via central neuromodulation (electrical epidural stimulation of the lumbo-sacral spinal cord) and exhibit moderate step heights and foot dragging. Superimposition of selective sciatic nerve stimulation allows to further gradually modulate the gait cycle and enhance the movement, for instance through increasing the step height of the stimulated leg (trajectories T2, at 30 Hz, and trajectories T3, at 70 Hz) with increased frequency, or reducing the foot dragging contralateral (trajectories T2', at 30 Hz, and trajectories T3', at 70 Hz). Peripheral nerve stimulation with graded frequencies gradually enhances the general stepping pattern of both the stimulated and the contralateral foot and allows thus, in combination with central neuromodulation, to improve controlled movement restoration.

The lower part of FIG. 6 relates to enhanced ipsilateral flexion and the foot trajectories are shown for EES stimulation only as trajectories T1 and also superimposed to that the trajectories T3 of PNS in addition to the EES stimulation.

The PNS stimulation is done in a range between 30 Hz (trajectories T2) to 70 Hz (trajectories T3).

The upper part of FIG. 6 relates to enhanced contralateral extension and the foot trajectories are shown for EES stimulation only as trajectories T1' also superimposed to that the trajectories T3' of PNS in addition to the EES stimulation.

The PNS stimulation is done in a range between 30 Hz (trajectories T2') to 70 Hz (trajectories T3').

Figure 7:
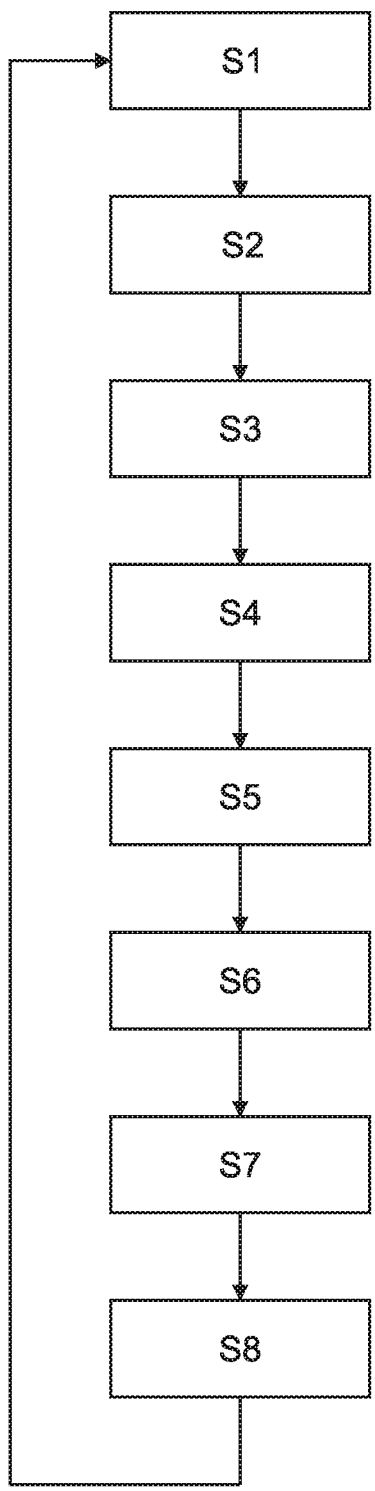
FIG. 7 shows a flow chart showing an example of how the embodiment according to the present disclosure of the neuromodulation and/or neurostimulation system is operated.

FIG. 7 relates to a flow chart showing an example how the closed-loop embodiment according to the present disclosure of the neuromodulation and/or neurostimulation system 10 is operated.

In step S1 physiological signals of the patient (or as shown in the example of FIG. 3-6 of a mammal, here a rat) are gained and recorded. This is done by the sensing unit 12.

In step S2 the gained signals are provided to the control unit 14.

In step S3 an initial stimulation parameter set is provided by the control unit 14.

In step S4 a matching of the stimulation control signals provided by the control unit 14 to control the PNS stimulation module 20 and/or the CNS stimulation module 18 with physiological signals related to a move intention of a subject decoded from its brain and/or nervous system is performed.

In step S5 a matching of the stimulation control signals provided by the control unit 14 to control the PNS stimulation module 20 and/or the CNS stimulation module 18 with a desired kinematic trajectory is performed.

In step S6 a matching of the stimulation control signals provided by the control unit 14 to control the PNS stimulation module 20 and/or the CNS stimulation module 18 with desired forces with respect to a surface, on which the subject is located or that the subject is touching is performed.

In step S7 a matching of the stimulation control signals provided by the control unit 14 to control the PNS stimulation module 20 and/or the CNS stimulation module 18 with muscle activation for certain gait patterns and/or grasp types and/or movements is performed.

Steps S4 to S7 can be performed sequentially or in parallel.

In step S8 a decoding of physiological signals is performed. This is done by the control unit 14, which is configured such that signals provided by the sensing unit 12 and related to movement of the subject can be decoded, especially continuously movement of the subject and/or signals related to force(s) and/or EMG activity and/or kinematic trajectories can be decoded.

As can be seen from the flow chart, the system 10 works as a closed-loop system in real-time.

After step S8 it is continued with step S1.

Note that the example control and estimation routines included herein can be used with various neuromodulation and/or neurostimulation system configurations. The control methods and routines disclosed herein may be stored as executable instructions in non-transitory memory and may be carried out by the control unit in combination with the various sensors, actuators, and other system hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the control unit, where the described actions are carried out by executing the instructions in a system including the various hardware components in combination with the electronic control unit.

REFERENCES

10 Neuromodulation and/or neuro stimulation system
12 ensing unit
12a Sensing unit
12b Sensing unit
12c Sensor
12d Sensor
14 Control unit
16 Stimulation unit
18 Central Nervous System (CNS) stimulation module
20 Peripheral Nervous System (PNS) stimulation module
22 Implantable Pulse Generator (IPG)
24 Implantable Pulse Generator (IPG)
25 Electrodes
26 Electrodes
10' System
14' Control Unit
18' Central Nervous System (CNS) stimulation module
20' Peripheral Nervous System (PNS) stimulation module
100 Rat
102 Spinal Cord (Rat)
104 Ankle Muscle
106 Bipolar Wire Electrode
107 Neural Polyimide-Based Multi-Channel Implant
108 Monopolar Wire Electrode
110 Monopolar Wire Electrode
112 Sciatic Nerve
114 Treadmill
116 Camera
P Patient
K1 Kinematic Crest Signal
K2 Kinematic Hip Signal
K3 Kinematic Knee Signal
K4 Kinematic Ankle Signal
K5 Kinematic Foot Signal
M Memory
ST stairs
S1 Method Step S1
S2 Method Step S2
S3 Method Step S3
S4 Method Step S4
S5 Method Step S5
S6 Method Step S6
S7 Method Step S7
S8 Method Step S8
T1 trajectory (EES only)
T2 trajectory
T3 trajectory
T1' trajectory (EES only)
T2' trajectory (EES and PNS with Hz)
T3' trajectory

The invention claimed is:

1. A neuromodulation and/or neurostimulation system comprising at least the following components:
at least one sensing unit, at least one control unit, at least one stimulation unit that comprises at least one Implantable Pulse Generator (IPG), at least one Central Nervous System (CNS) stimulation module comprising electrodes for providing CNS stimulation configured to evoke at least one of a gait pattern, grasp type, or movement, at least one Peripheral Nervous System (PNS) stimulation module comprising electrodes for providing PNS stimulation configured to refine the evoked at least one of the gait pattern, grasp type, or movement; and wherein the IPG is at least one of the components of the neuromodulation and/or neurostimulation system that is implantable;
wherein the at least one control unit is configured to:
during a treatment,
provide the CNS stimulation via the CNS stimulation module, and
provide the PNS stimulation with different stimulation frequencies, wherein the PNS stimulation directly stimulates muscles via the PNS stimulation module.

2. The system according to claim 1, wherein the CNS stimulation module is or comprises an epidural stimulation module capable to provide epidural spinal stimulation.

3. The system according to claim 1, wherein the PNS stimulation module is a Functional Electrical Stimulation (FES) module capable to provide electrical stimulation of peripheral nerves.

4. The system according to claim 1, wherein the components of the neuromodulation and/or neurostimulation system form a closed-loop system.

5. The system according to claim 1, wherein the components of the neuromodulation and/or neurostimulation system form an open-loop system.

6. The system according to claim 1, wherein the control unit is configured such that control is done in real-time.

7. The system according to claim 1, wherein at least one electrode of the electrodes for the PNS module has at least one fixation element for anchoring the at least one electrode in or to surrounding structures.

8. The system according to claim 1, wherein the control unit is configured such that based on sensing signals provided and gained by means of the sensing unit, the PNS stimulation provided by the PNS stimulation module and/or the CNS stimulation provided by CNS stimulation module can be adjusted and/or adapted to: at least partially match stimulation control signals provided by the control unit to control the PNS stimulation module and/or the CNS stimulation module with physiological signals related to a move intention of a subject decoded from its brain and/or nervous system, and/or at least partially match the stimulation control signals provided by the control unit to control the PNS stimulation module and/or the CNS stimulation module with a desired kinematic trajectory, and/or at least partially match the stimulation control signals provided by the control unit to control the PNS stimulation module and/or the CNS stimulation module with desired forces with respect to a surface on which the subject is located or that the subject is touching.

9. The system according to claim 8, wherein the control unit is configured such that the sensing signals provided by the sensing unit can be decoded;
wherein the sensing signals are related to movement of the subject; and wherein movement of the subject includes one or more of continuous movement of the subject, signals related to force(s), EMG activity, and/or kinematic trajectories.

10. The system according to claim 1, wherein the control unit is configured such that the PNS stimulation provided by the PNS stimulation module and the CNS stimulation provided by the CNS stimulation module during the treatment is at least partially interleaved.

11. The system according to claim 1, wherein the control unit is configured such that the PNS stimulation provided by the PNS stimulation module and the CNS stimulation provided by the CNS stimulation module during the treatment is at least partially superimposed; and
wherein the control unit is configured such that the different frequencies provided during the PNS stimulation is within a frequency range.

12. A method of providing neuromodulation and/or neurostimulation to a patient having a spinal cord injury, comprising:
providing Central Nervous System (CNS) stimulation configured to evoke at least one of a gait pattern, grasp type, or movement combined with Peripheral Nervous System (PNS) stimulation configured to refine the evoked at least one of the gait pattern, grasp type, or movement, by using a neuromodulation and/or neurostimulation system, the neuromodulation and/or neurostimulation system comprising at least the following components:
at least one sensing unit, at least one control unit, at least one stimulation unit, at least one Central Nervous System (CNS) stimulation module for providing the CNS stimulation, at least one Peripheral Nervous System (PNS) stimulation module for providing the PNS stimulation; wherein at least one of the components of the neuromodulation and/or neurostimulation system is implantable or at least partially implantable; and
wherein the PNS stimulation directly stimulates muscles, and
wherein providing the CNS stimulation combined with the PNS stimulation includes providing the PNS stimulation at different frequencies.

13. The method of claim 12, wherein the CNS stimulation comprises epidural spinal stimulation below a level of the spinal cord injury.

14. The method of claim 12, wherein the control unit is configured such that based on sensing signals provided and gained by means of the sensing unit, the PNS stimulation provided by the PNS stimulation module and/or the CNS stimulation provided by CNS stimulation module can be adjusted and/or adapted to:
at least partially match stimulation control signals provided by the control unit to control the PNS stimulation module and/or the CNS stimulation module with physiological signals related to a move intention of a subject decoded from its brain and/or nervous system, and/or at least partially match the stimulation control signals provided by the control unit to control the PNS stimulation module and/or the CNS stimulation module with a desired kinematic trajectory, and/or at least partially match the stimulation control signals provided by the control unit to control the PNS stimulation module and/or the CNS stimulation module with desired forces with respect to a surface on which the subject is located or that the subject is touching; and wherein the control unit is configured such that the sensing signals provided by the sensing unit can be decoded, the sensing signals related to movement of the subject, and wherein movement of the subject includes one or more of continuous movement of the subject, signals related to force(s), EMG activity, and/or kinematic trajectories.

15. The method of claim 12, wherein the control unit is configured such that the PNS stimulation provided by the PNS stimulation module and the CNS stimulation provided by the CNS stimulation module is at least partially interleaved or at least partially superimposed; and
wherein the different frequencies are within a frequency range.

16. The method of claim 12, wherein the CNS stimulation activates afferent sensory neurons entering the spinal cord of the patient.

17. The method of claim 12, wherein the control unit is capable to independently control and switch on and off either the PNS stimulation module or the CNS stimulation module.

18. The method of claim 12, wherein the CNS stimulation does not directly stimulate motor-neurons.

* * * * *